United States Patent
Muller

(10) Patent No.: US 10,315,238 B1
(45) Date of Patent: Jun. 11, 2019

(54) TESTING SUBTERRANEAN WATER FOR A HAZARDOUS WASTE MATERIAL REPOSITORY

(71) Applicant: Deep Isolation, Inc., Berkeley, CA (US)

(72) Inventor: Richard A. Muller, Berkeley, CA (US)

(73) Assignee: Deep Isolation, Inc., Berkeley, CA (US)

( * ) Notice: Subject to any disclaimer, the term of this patent is extended or adjusted under 35 U.S.C. 154(b) by 0 days.

(21) Appl. No.: 16/181,616

(22) Filed: Nov. 6, 2018

(51) Int. Cl.
| | |
|---|---|
| B09B 1/00 | (2006.01) |
| G21F 9/36 | (2006.01) |
| G01N 33/24 | (2006.01) |
| G21F 5/008 | (2006.01) |
| G21F 5/14 | (2006.01) |
| E21B 41/00 | (2006.01) |
| E21B 43/00 | (2006.01) |
| E21B 49/08 | (2006.01) |
| G01T 1/169 | (2006.01) |

(52) U.S. Cl.
CPC ............ *B09B 1/008* (2013.01); *E21B 41/005* (2013.01); *E21B 43/00* (2013.01); *E21B 49/08* (2013.01); *G01N 33/246* (2013.01); *G01T 1/169* (2013.01); *G21F 5/008* (2013.01); *G21F 5/14* (2013.01); *G21F 9/36* (2013.01); *E21B 2049/085* (2013.01)

(58) Field of Classification Search
CPC ...................................................... B09B 1/008
See application file for complete search history.

(56) References Cited

U.S. PATENT DOCUMENTS

| | | | |
|---|---|---|---|
| 5,165,235 A | 11/1992 | Nitschke | |
| 5,340,235 A | 8/1994 | Milliken | |
| (Continued) | | | |

FOREIGN PATENT DOCUMENTS

| | | |
|---|---|---|
| WO | WO92007667 | 5/1992 |
| WO | WO2015069300 | 5/2015 |
| WO | WO2016/177876 | 11/2016 |

OTHER PUBLICATIONS

Muller, R. "Radioisotope Dating with a Cyclotron," Science, vol. 196, No. 4289, dated Apr. 29, 1977, 6 pages.

(Continued)

*Primary Examiner* — Janine M Kreck
(74) *Attorney, Agent, or Firm* — Fish & Richardson P.C.

(57) ABSTRACT

Techniques for testing subterranean water for one or more radioactive isotopes for a hazardous waste material repository include collecting, from a test drillhole formed from a terranean surface to a subterranean formation, a subterranean water sample from the subterranean formation; determining, with an accelerator mass spectrometry (AMS) system, a concentration of a radioactive isotope of an element in the subterranean water sample relative to a stable isotope of the element in the subterranean water sample; comparing the determined concentration of the radioactive isotope of the element in the subterranean water sample with a concentration of the radioactive isotope of the element in a surface water sample relative to the stable isotope of the element in the surface water sample; and based on the determined concentration of the radioactive isotope in the subterranean water sample being a specified percentage of the concentration of the radioactive isotope in the surface water sample, determining that the subterranean formation is a hazardous waste storage repository.

37 Claims, 5 Drawing Sheets

(56) References Cited

U.S. PATENT DOCUMENTS

| | | | |
|---|---|---|---|
| 5,377,104 | A | 12/1994 | Sorrells |
| 5,387,741 | A | 2/1995 | Shuttle |
| 5,850,614 | A | 12/1998 | Crichlow |
| 5,863,283 | A | 1/1999 | Gardes |
| 6,238,138 | B1 | 5/2001 | Crichlow |
| 7,287,934 | B2 | 10/2007 | Okutsu |
| 8,933,289 | B2 | 1/2015 | Crichlow |
| 10,002,683 | B2 | 6/2018 | Muller et al. |
| 2002/0020528 | A1 | 2/2002 | McCabe |
| 2010/0105975 | A1 | 4/2010 | Baird |
| 2011/0005762 | A1 | 1/2011 | Poole |

OTHER PUBLICATIONS

Wikipedia.com [online], "Accelerator Mass Spectrometry," Apr. 9, 2018, [retirved on Aug. 27, 2018] retirved from: http://en.wikipedia.org/wiki/Accelerator_mass_spectrometry, 3 pages.

[No Author] World Nuclear News, "Yucca Mountain cost estimate rises to $96 billion", Aug. 6, 2008, 2 pages, ISSN 2040-5766.

Bill W. Arnold, et al., "Reference Design and Operations of Deep Borehole Disposal of High-Level Radioactive Waste," Sandia National Laboratories (2011) ("Sandia Report") (available at: http://prod.sandia.gov/techlib/access-control.cgi/2011/116749.pdf).

Christopher Ian Hoag, "Canister Design for Deep Borehole Disposal of Nuclear Waste," Massachusetts Institute of Technology, May 2006 (pp. 1-6).

Cornwall, W., "Deep Sleep. Boreholes drilled into Earth's crust get a fresh look for nuclear waste disposal," Science, vol. 349, Issue 6244, Jul. 10, 2015, 132-35.

Faybishenko et al., Editors, Lawrence Berkeley National Laboratory and Sandia National Laboratories: "International Approaches for Deep Geological Disposal of Nuclear Waste: Geological Challenges in Radioactive Waste Isolation", prepared for the US Department of Energy, Fifth Worldwide Review—2016, 474 pages.

Frances Elizabeth Dozier, "Feasibility of Very Deep Borehole Disposal of US Nuclear Defense Wastes," Massachusetts Institute of Technology, Sep. 2011 (pp. 1-12).

Gibb et al., "A Model for Heat Flow in Deep Borehole Disposals of High-Level Nuclear Waste," Journal of Geophysical Research, vol. 113, dated May 6, 2008, 18 pages.

Hiroki Sone and Mark D. Zoback, "Mechanical properties of shale-gas reservoir rocks—Part 1:Static and dynamic elastic properties and anisotropy," Geophysics, vol. 78, No. 5, Sep. Oct. 2013, D381-92.

International Search Report and Written Opinion issued in International Application No. PCT/US2016/066539, dated Apr. 19, 2017, 13 pages.

J. Winterle et al., Regulatory Perspectives on Deep Borehole Disposal Concepts, prepared for the U.S. Nuclear Regulatory Commission, Contract NRC-02-07006, Center for Nuclear Waste Regulatory Analyses, San Antonio, TX, May 2011, 24 pages.

Johnathan Sutton Gibbs, "Feasibility of Lateral Emplacement in Very Deep Borehole Disposal of High Level Nuclear Waste" master's thesis, Massachusetts Institute of Technology (2010) ("Gibbs") (available at: https://dspace.mit.edu/handle/1721.1/63242), 2 pages.

Neuzil et al., "Shale: An overlooked option forUS nuclear waste disposal," Bulletin of the Atomic Scientists Nov. 2014, Retrieved from the Internet: http://thebulletin .org/shale-overlooked-option-us-nuclear-waste-disposal7831 printed Sep. 26, 2016, 5 pages.

Neuzil, "Can Shale Safely Host U.S. Nuclear Waste?" EOS. vol. 94, No. 30, Dated Jul. 23, 2013, 3 pages.

PCT Notification of Transmittal of the International Search Report and Written Opinion in International Application No. PCT/US2018/035974, dated Aug. 24, 2018, 13 pages.

U.S. Nuclear Waste Technical Review Board, A Report to the U.S. Congress and the Secretary of Energy, Evaluation of Technical Issues Associated With the Development of a Separate Repository for U.S. Department of Energy-Managed High-Level Radioactive Waste and Spent Nuclear Fuel (2015) ("NWTRB") (available at: http://www.nwtrb.gov/reports/disposal_options.pdf).

Vartabedian, Ralph; "Decades-old war over Yucca Mountain nuclear dump resumes under Trump budget plan", Mar. 29, 2017, ralph.vartabdian@latimes.com; twitter @rvartabedian; 4 pages.

YuccaMountain.org; Eureka County, Nevada—Nuclear Waste Office, FAQ, Eureka County Home, last updated Mar. 17, 2017; 12 pages.

TESTING SUBTERRANEAN WATER FOR A HAZARDOUS WASTE MATERIAL REPOSITORY

TECHNICAL FIELD

This disclosure relates to testing subterranean water and, more particular, testing subterranean water for one or more radioactive isotopes for a hazardous waste material repository.

BACKGROUND

Storing hazardous waste material underground may have significant risks. One risk may be that the hazardous waste material, or byproducts of the hazardous waste material, may enter into a source of human-consumable water. Some subterranean formations allow mobile water; that is the movement of water stored in the formation to a location in which human-consumable water is located. Therefore, any hazardous waste material stored underground must be kept from a source of mobile water.

SUMMARY

In a general implementation, a method includes collecting, from a test drillhole formed from a terranean surface to a subterranean formation, a subterranean water sample from the subterranean formation; determining, with an accelerator mass spectrometry (AMS) system, a concentration of a radioactive isotope of an element in the subterranean water sample relative to a stable isotope of the element in the subterranean water sample; comparing the determined concentration of the radioactive isotope of the element in the subterranean water sample with a concentration of the radioactive isotope of the element in a surface water sample relative to the stable isotope of the element in the surface water sample; and based on the determined concentration of the radioactive isotope in the subterranean water sample being a specified percentage of the concentration of the radioactive isotope in the surface water sample, determining that the subterranean formation includes a hazardous waste storage repository.

In an aspect combinable with the general implementation, the radioactive isotope is carbon-14 ($^{14}C$) and the stable isotope is $^{12}C$ or $^{13}C$; the radioactive isotope is chlorine-36 ($^{36}Cl$) and the stable isotope is $^{35}Cl$; the radioactive isotope is iodine-129 ($^{129}I$) and the stable isotope is $^{127}I$; the radioactive isotope is beryllium-10 ($^{10}Be$) and the stable isotope is $^{9}Be$; or the radioactive isotope is aluminum-26 ($^{26}Al$) and the stable isotope is $^{27}Al$.

In an aspect combinable with any of the previous aspects, the specified percentage is less than 50 percent.

An aspect combinable with any of the previous aspects further includes collecting the surface water sample from a surface water source.

In an aspect combinable with any of the previous aspects, the surface water source includes at least one of an aquifer or a water source at the terranean surface in contact with the earth's atmosphere.

In an aspect combinable with any of the previous aspects, the surface water sample includes potable water.

In an aspect combinable with any of the previous aspects, collecting the subterranean water sample from the subterranean formation includes operating a downhole tool in the test drillhole to collect a core sample from the subterranean formation; retrieving the core sample to the terranean surface; and removing water from the core sample, the removed water including the subterranean water sample.

In an aspect combinable with any of the previous aspects, collecting the subterranean water sample from the subterranean formation is performed prior in time to collecting the subterranean water sample from the subterranean formation.

In an aspect combinable with any of the previous aspects, the subterranean formation includes a shale formation.

In an aspect combinable with any of the previous aspects, the subterranean formation includes a permeability of less than about 0.01 millidarcys.

An aspect combinable with any of the previous aspects further includes forming the test drillhole from the terranean surface to the subterranean formation.

In an aspect combinable with any of the previous aspects, the test drillhole includes a vertical drillhole.

In an aspect combinable with any of the previous aspects, the subterranean formation includes a brittleness of less than about 10 MPa, where brittleness includes a ratio of compressive stress of the subterranean formation to tensile strength of the subterranean formation.

In an aspect combinable with any of the previous aspects, the subterranean formation includes about 20 to 40% weight by volume of clay or organic matter.

In an aspect combinable with any of the previous aspects, the subterranean formation includes an impermeable layer.

In an aspect combinable with any of the previous aspects, the subterranean formation includes a leakage barrier defined by a time constant for leakage of a hazardous waste material of 10,000 years or more.

In an aspect combinable with any of the previous aspects, the subterranean formation includes a hydrocarbon or carbon dioxide bearing formation.

An aspect combinable with any of the previous aspects further includes initiating creation of the hazardous waste storage repository in or under the subterranean formation.

In an aspect combinable with any of the previous aspects, initiating creation of the hazardous waste storage repository in or under the subterranean formation includes forming an access drillhole from the terranean surface toward the subterranean formation; and forming a storage drillhole coupled to the access drillhole in or under the subterranean formation, the storage drillhole including a hazardous waste storage area.

In an aspect combinable with any of the previous aspects, the access drillhole includes a vertical drillhole.

In an aspect combinable with any of the previous aspects, the access drillhole is the test drillhole.

In an aspect combinable with any of the previous aspects, the storage drillhole includes a curved portion and a horizontal portion.

In an aspect combinable with any of the previous aspects, the subterranean formation includes a thickness proximate the hazardous waste material storage area of at least about 200 feet.

In an aspect combinable with any of the previous aspects, the subterranean formation includes a thickness proximate the hazardous waste material storage area that inhibits diffusion of a hazardous waste material through the subterranean formation for an amount of time that is based on a half-life of the hazardous waste material.

An aspect combinable with any of the previous aspects further includes installing a casing in the access drillhole and the storage drillhole that extends from at or proximate the terranean surface, through the access drillhole and the storage drillhole, and into the hazardous waste material storage area of the storage drillhole.

An aspect combinable with any of the previous aspects further includes cementing the casing to the access drillhole and the storage drillhole.

An aspect combinable with any of the previous aspects further includes, subsequent to forming the access drillhole, producing hydrocarbon fluid from the subterranean formation, through the access drillhole, and to the terranean surface.

An aspect combinable with any of the previous aspects further includes storing hazardous waste material in the hazardous waste storage area.

In an aspect combinable with any of the previous aspects, storing hazardous waste material in the hazardous waste storage area includes moving a storage canister through an entry of the access drillhole that extends into the terranean surface, the entry at least proximate the terranean surface, the storage canister including an inner cavity sized to enclose the hazardous waste material; moving the storage canister through the access drillhole and into the storage drillhole; and moving the storage canister through the storage drillhole to the hazardous waste storage area.

An aspect combinable with any of the previous aspects further includes forming a seal in at least one of the access drillhole or the storage drillhole that isolates the hazardous waste storage area from the entry of the access drillhole.

In an aspect combinable with any of the previous aspects, the hazardous waste material includes spent nuclear fuel or other radioactive material.

In an aspect combinable with any of the previous aspects, the storage canister includes a connecting portion configured to couple to at least one of a downhole tool string or another storage canister.

An aspect combinable with any of the previous aspects further includes monitoring the hazardous waste material stored in the hazardous waste material storage area of the storage drillhole.

In an aspect combinable with any of the previous aspects, monitoring the hazardous waste material stored in the hazardous waste material storage area of the storage drillhole includes removing the seal; and retrieving the storage canister from the hazardous waste material storage area to the terranean surface.

In an aspect combinable with any of the previous aspects, monitoring the hazardous waste material stored in the hazardous waste material storage area of the storage drillhole includes monitoring at least one variable associated with the storage canister from a sensor positioned proximate the hazardous waste material storage area; and recording the monitored variable at the terranean surface.

In an aspect combinable with any of the previous aspects, the monitored variable includes at least one of radiation level, temperature, pressure, presence of oxygen, presence of water vapor, presence of liquid water, acidity, or seismic activity.

An aspect combinable with any of the previous aspects further includes, based on the monitored variable exceeding a threshold value removing the seal; and retrieving the storage canister from the hazardous waste material storage drillhole portion to the terranean surface.

Implementations of subterranean water testing systems and methods according to the present disclosure may also include one or more of the following features. For example, subterranean water testing systems and methods according to the present disclosure may be used to identify or determine that a particular subterranean formation is suitable as a hazardous waste material repository. The determined hazardous waste material repository may be used to store hazardous waste material, such as spent nuclear fuel, isolated from human-consumable water sources. The determined hazardous waste material repository may be suitable for storing the hazardous waste material for durations of time up to, for example, 1,000,000 years. As another example, subterranean water testing systems and methods according to the present disclosure may confirm that a particular geologic formation is suitable as a hazardous waste material repository.

The details of one or more implementations of the subject matter described in this disclosure are set forth in the accompanying drawings and the description below. Other features, aspects, and advantages of the subject matter will become apparent from the description, the drawings, and the claims.

DETAILED DESCRIPTION

Figure 1:
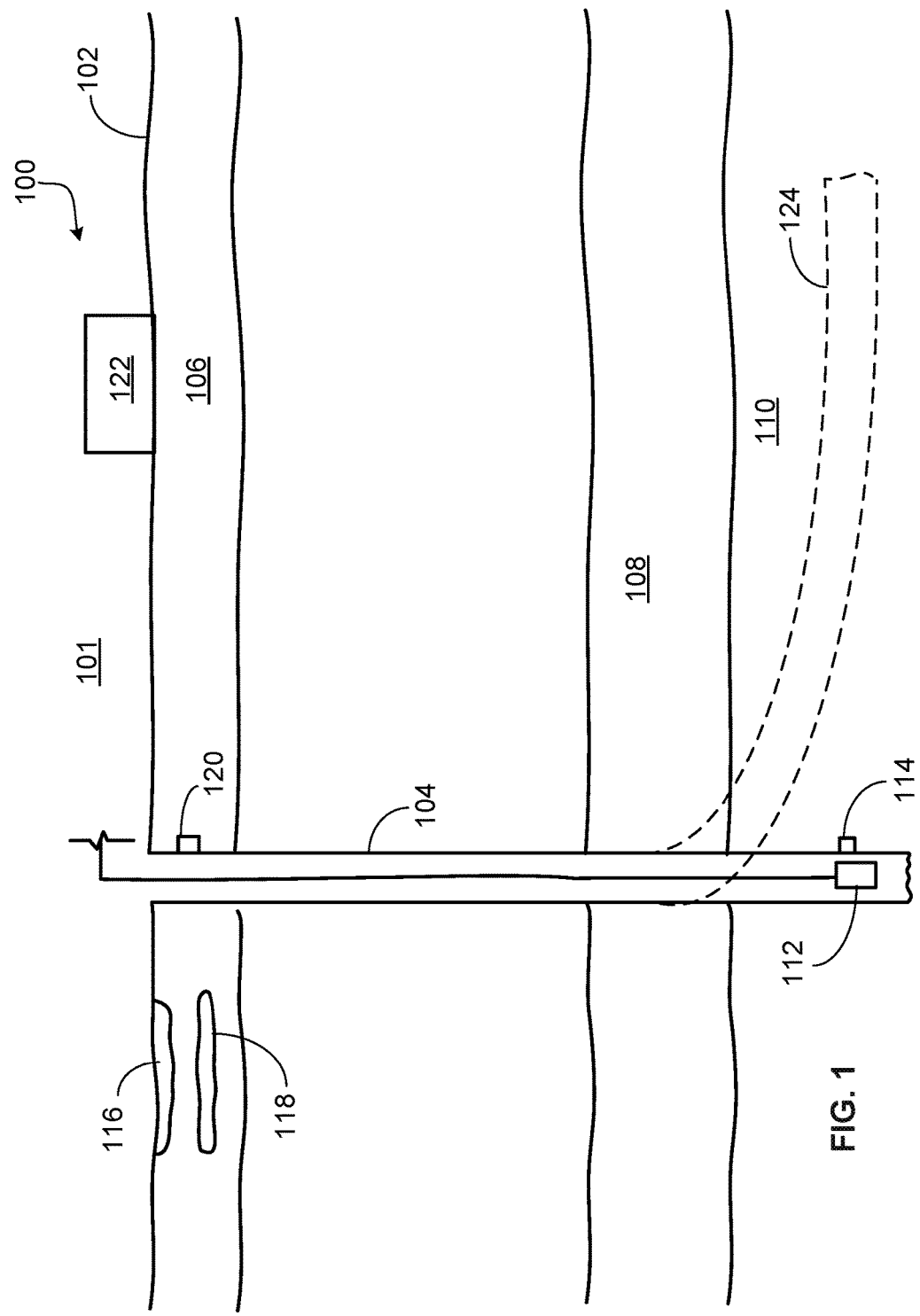
FIG. 1 is a schematic illustration of an example implementation of a subterranean water testing system according to the present disclosure.

FIG. 1 is a schematic illustration of an example implementation of a subterranean water testing system 100. As shown in this example, the system 100 includes a test drillhole 104 formed from a terranean surface 102, through a surface water formation 106, and into and through subterranean formations 108 and 110 that are deeper than the surface water formation 106. Each of the formations 106, 108, and 110 may comprise a geologic formation formed of one or more rock types, as well as water (e.g., fresh or brine) and in some cases other fluids (e.g., hydrocarbon fluids). In this example, the test drillhole 104 is shown as a vertical drillhole. However, in alternative implementations, a directional drillhole 124 (shown in dashed line) may be formed and used in the system 100 in place of (or in addition to) the test drillhole 104) according to the present disclosure.

The surface water formation 106, in this example, is a geologic layer comprised of one or more layered rock formations and includes one or more surface water sources. For example, surface water formation 106 may include one or more open water sources 116 (e.g., lakes, ponds, rivers, creeks). In some aspects, open water sources 116 are water sources that have direct contact with the atmosphere 101. Surface water formation 106 may also include one or more aquifers 118 that are not in direct contact with the atmosphere 101 but are suitable for human consumption (e.g., with or without conventional water treatment). Thus, in this example implementation of system 100, surface water includes both open water sources 116 and aquifers 118.

Examples of rock formations of which the surface water formation 106 may be composed include porous sandstones and limestones, among other formations.

Below the surface water formation 106, in this example implementation, are subterranean formations 108 and 110. One or both of the subterranean formations 108 or 110 may include or hold subterranean water. Subterranean water, in this example system, is water that is not an open water source or aquifer and is not in present-day contact with the atmosphere 101 (but may have been at some time in the past). In some aspects, subterranean water is non-potable or is not fit for human consumption (or both). System 100 may be used (e.g., as described with reference to FIG. 3 and process 300) to test one or both of subterranean formations 108 or 110 for hazardous waste material storage according to the subterranean water found in such formations.

System 100 also includes a downhole tool 112 (e.g., a core drill) that can be conveyed into the test drillhole 104 and to one or all of formations 106, 108, and 110 to procure a core sample 114 or core sample 120. In this example, core sample 114 include subterranean water while core sample 120 includes surface water. Thus, a subterranean water sample may be obtained from core sample 114, while a surface water sample may be obtained from core sample 120 (or open water source 116 or aquifer 118). Although core sample 114 is shown as being obtained from subterranean formation 110, one or more core samples 114 may be obtained from this formation or subterranean formation 108 (or both).

System 100 also includes an accelerator mass spectrometry system (AMS) 122. The AMS system 122, generally, may be operated to perform many testing functions. For example, the AMS system 122 may analyze substances, such as water, to detect naturally occurring, long-lived radio-isotopes (of elements) such as beryllium-10 ($^{10}$Be), chlorine-36 ($^{36}$Cl), aluminum-26 ($^{26}$Al), iodine-129 ($^{129}$I), and carbon-14 (i.e., radiocarbon or $^{14}$C) in such substances. In some cases, certain radioactive isotopes, such as $^{36}$Cl and $^{129}$I, may be produced in the atmosphere 101 by cosmic radiation, and mixed with surface water, or is produced directly in the surface water or surface rock. Thus, substances such as surface water sources may have a particular concentration of such radioactive isotopes of the elements based on time period of the atmosphere 101 to which the substances have been exposed. Substances no longer exposed to the atmosphere 101, such as subterranean water, experience a decay in the concentration of such radioactive isotopes (e.g., $^{36}$Cl relative to the concentration of the stable isotope, $^{37}$Cl, of the element chlorine; $^{129}$I relative to the concentration of the stable isotope, $^{127}$I, of the element iodine; $^{10}$Be relative to the concentration of the stable isotope, $^{9}$Be, of the element beryllium; $^{14}$C relative to the concentration of the stable isotopes, $^{12}$C or $^{13}$C, of the element carbon; $^{26}$Al relative to the concentration of the stable isotope, $^{27}$Al, of the element aluminum) as time passes without such exposure. Thus, a measure of a concentration of radioactive isotopes in a substance, such as subterranean water, may also indicate an amount of time that has passed since the substance was last exposed to the atmosphere 101 or surface water.

Figure 3:
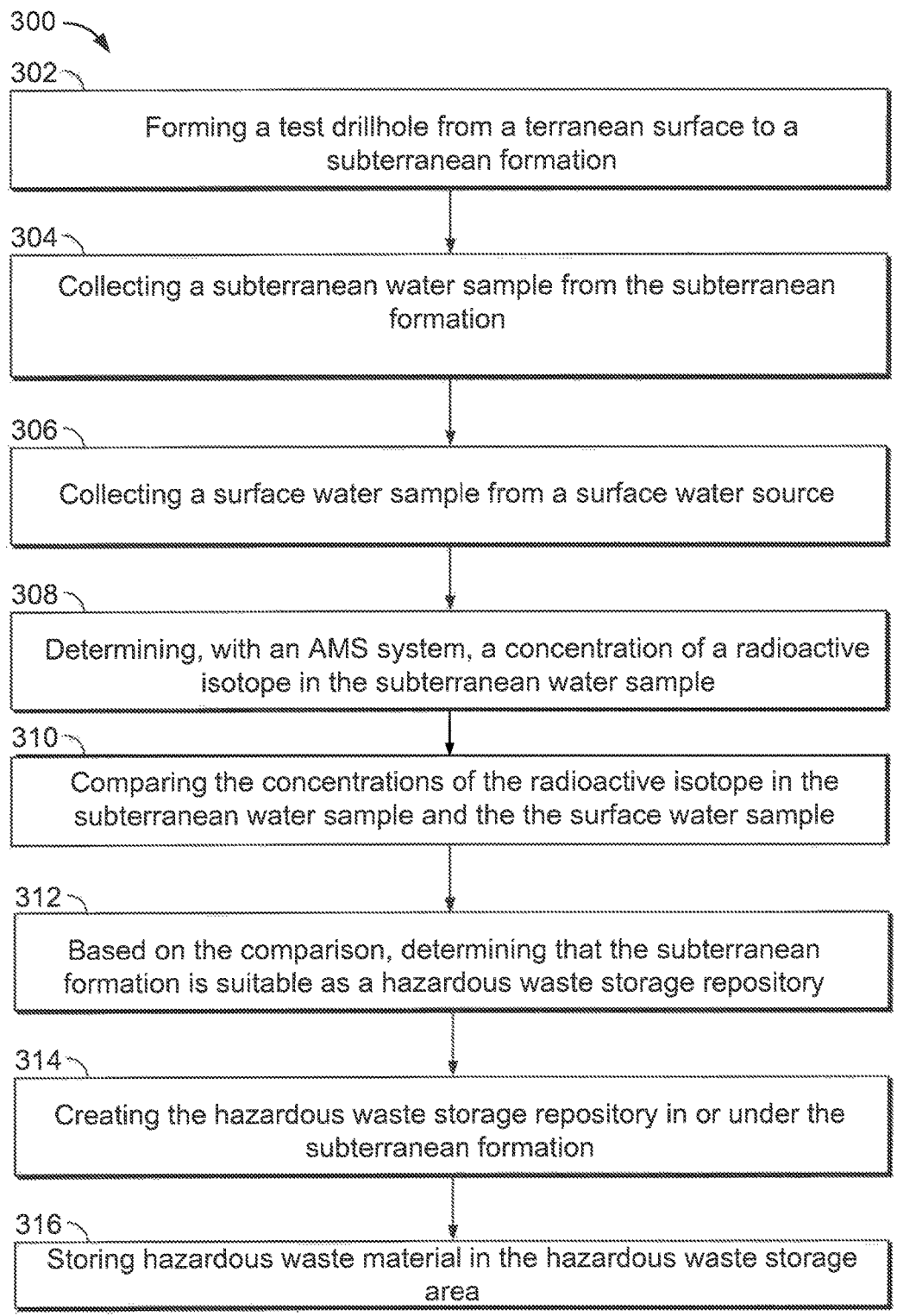
FIG. 3 is a flowchart that illustrates an example process for testing subterranean water for a ratio of a radioactive isotope of a particular element with respect to a stable isotope of the particular element.

Turning now to FIG. 3, a flowchart that illustrates an example process 300 for testing subterranean water for a ratio of a radioactive isotope of a particular element with respect to a stable isotope of the particular element is shown. Process 300 may be performed with the system 100. Process 300 begins at step 302, which includes forming a test drillhole from a terranean surface to a subterranean formation. For example, the test drillhole 104 may be drilled or otherwise formed from the terranean formation to one or both of the subterranean formations 108 or 110. Test drillhole 104, may be relatively smaller (e.g., in diameter) than a wellbore formed for the purpose of producing hydrocarbons. Alternatively, test drillhole 104 may be similar to a wellbore formed for the purpose of producing hydrocarbon and, in some aspects, may have had hydrocarbons produced therefrom previous to step 302.

Process 300 continues at step 304, which includes collecting a subterranean water sample from the subterranean formation. In some aspects, subterranean water may be naturally collected in a downhole end of the drillhole 104 due to, e.g., a pressure difference between one or both of subterranean formation 108 or 110 and the test drillhole 104 (i.e., the formations at a higher fluid pressure than the test drillhole 104). In some aspects, the downhole tool 112, e.g., a core drill, may be operated to obtain core sample 114 which includes subterranean water. In some aspects, the core sample 114 may have been previously obtained—or a subterranean water sample may have been previously collected from one or both of formations 108 or 110—prior to the initiation of process 300 (e.g., eternal to system 100). Thus, "collecting" in step 304 may include or mean identifying a previously gathered subterranean water sample.

Process 300 continues at step 306, which includes collecting a surface water sample from a surface water source. For example, surface water may be collected from one or both of open water sources 116 or aquifers 118. A surface water sample may also be collected from core sample 120 in surface water formation 106. In some aspects, a surface water sample may have been previously collected prior to the initiation of process 300 (e.g., eternal to system 100). Thus, "collecting" in step 306 may include or mean identifying a previously gathered subterranean water sample, or identifying a previously determined value of the concentration of the radioactive isotope relative to the stable isotope of the element in the surface water. In some aspects, the surface water sample can be sampled from a surface water source. Alternatively, the concentration of the radioactive isotope (such as $^{129}$I) compared to that of the stable isotope (for this case, $^{127}$I) can be determined from prior measurements) e.g., prior to the execution of process 300) of these ratios taken from surface water.

Process 300 continues at step 308, which includes determining, with an AMS system, a concentration of a radioactive isotope in the subterranean water sample. For example, AMS system 122 may be operated to determine a concentration of a particular radioactive isotope, such as $^{36}$Cl or $^{129}$I (or both), in the subterranean water sample (e.g., relative to a corresponding stable isotope of that element). In some aspects, step 308 may also include determining the concentration of the particular radioactive isotope in the surface water sample as well. Alternatively, the concentration of the radioactive isotope in the surface water sample may be known (e.g., previous to initiation of the process 300). In some examples, the determination of the concentration of the radioactive isotope with the AMS system includes measuring a ratio of the radioactive isotope (e.g., $^{36}$Cl or $^{129}$I) in the particular water sample to a stable (non-radioactive) isotope (e.g., $^{35}$Cl or $^{127}$I) of the same element (chlorine or iodine, respectively). Thus, reference to determining a concentration of the radioactive element means, in some aspects, determining a ratio of the radioactive isotope to the stable (non-radioactive) isotope of the same element in the particular (surface or subterranean, or both) sample.

Process 300 continues at step 310, which includes comparing the concentrations of the radioactive isotope in the subterranean water sample and the surface water sample. For example, once the concentrations of the particular isotope or isotopes are determined in surface and subterranean water samples (e.g., relative to a corresponding stable isotope of that element), they are compared to determine a difference between the two concentrations. For example, generally, the concentrations of $^{36}Cl$ and $^{129}I$ are higher in the surface water sample than the subterranean water sample due the atmosphere 101 that was in more recent contact with the surface water sample compared to the subterranean water sample.

Process 300 continues at step 312, which includes, based on the comparison, determining that the subterranean formation is suitable as a hazardous waste storage repository. For example, criteria for determining that the subterranean formation (108 or 110 or both) is suitable for the long-term (e.g., 100, 1000, 10,000 years or more) storage of hazardous waste material (e.g., spent nuclear fuel) may be the presence of water that has not been exposed to the atmosphere 101 for a particular duration of time, thereby evidencing the subterranean formation as a geologic formation which does not permit mobile water therethrough, or otherwise allow a flow of liquid from the formation toward the surface water formation 106. Such evidence may be proof of the subterranean formation to store hazardous waste material with little to no chance of such material mixing or polluting potable water fit for human consumption at the surface water formation 106.

In the example of $^{36}Cl$, this radioactive isotope has a half-life of 310,000 years. Due to the exposure to the atmosphere 101, $^{36}Cl$ is produced in the surface water sample. Subterranean water, however, is not in contact with the atmosphere 101 and therefore, any $^{36}Cl$ in the subterranean water sample decays (e.g., from the moment the water is no longer in contact with the atmosphere 101. After one half-life, half of the $^{36}Cl$ has decayed from (and is no longer in) the subterranean water sample. After two half-lives, half of the remaining $^{36}Cl$ has decayed from (and is no longer in) the subterranean water sample.

Therefore, in some examples, the subterranean formation (108, 110, or both) may be suitable as a hazardous waste material repository based on the concentration of the particular radioactive isotope (e.g., $^{36}Cl$ or $^{129}I$) in the subterranean water sample being a specified percentage of the concentration of the particular radioactive isotope (e.g., $^{36}Cl$ or $^{129}I$) in the surface water sample. The specified percentage, in some examples, is between 10 and 50%. Using $^{36}Cl$ as an example, for 50% as the specified percentage of the concentration in the subterranean water sample, the time duration since the subterranean water sample last was exposed to the atmosphere 101 is about 310,000 years (i.e., one half-life). For 25% as the specified percentage of the concentration in the subterranean water sample, the time duration since the subterranean water sample last was exposed to the atmosphere 101 is about 620,000 years (i.e., two half-lives). For 12.5% as the specified percentage of the concentration in the subterranean water sample, the time duration since the subterranean water sample last was exposed to the atmosphere 101 is about 930,000 years (i.e., three half-lives). For 10.6% as the specified percentage of the concentration in the subterranean water sample, then the time duration since the subterranean water sample last was exposed to the atmosphere 101 is about 1,000,000 years. Thus, the specified percentage may be set to a particular value based on a desired amount of time that represents the time duration since the subterranean water sample last was exposed to the atmosphere 101. If the specified percentage is met, then the subterranean formation from which the subterranean water sample was obtained may be determined to be a suitable hazardous waste material repository.

Figure 2A:
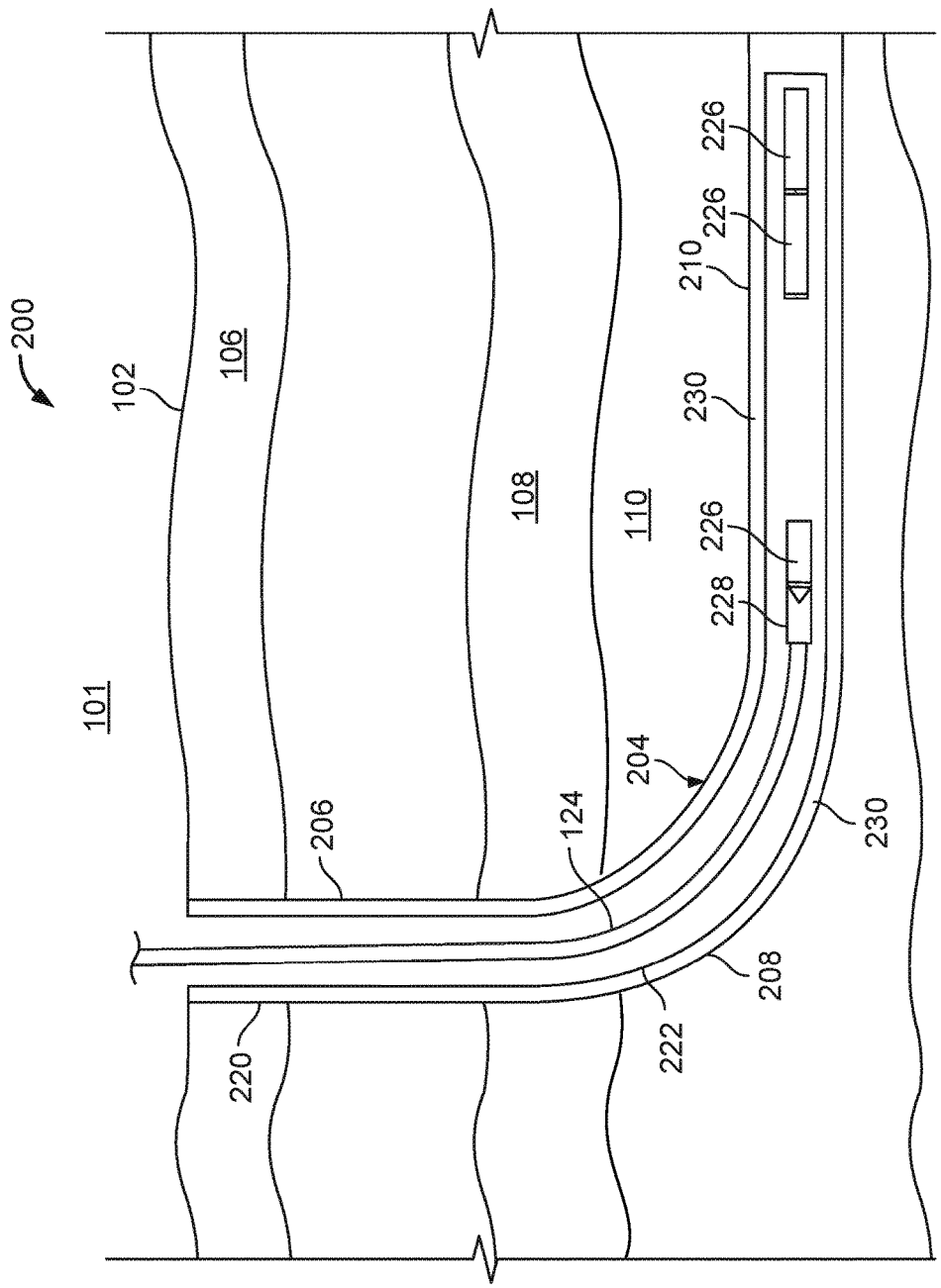
FIG. 2A is a schematic illustration of an example implementation of a hazardous waste material storage repository system during a deposit or retrieval operation according to the present disclosure.

Process 300 continues at step 314, which includes creating the hazardous waste storage repository in or under the subterranean formation. For example, a hazardous waste repository may be created as shown in FIG. 2A for example, which illustrates an example implementation of a hazardous waste material repository 200.

Figure 4:
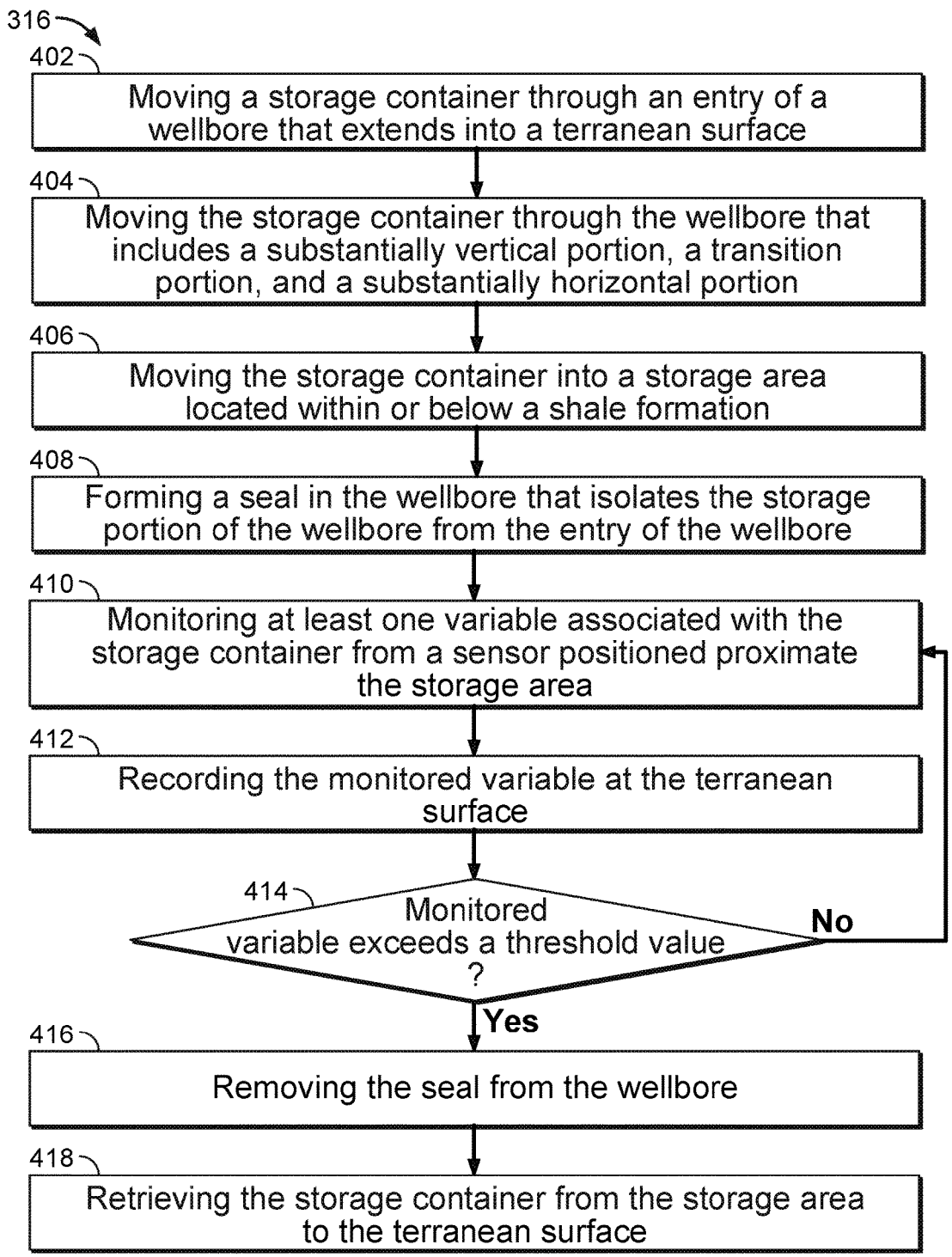
FIG. 4 is a flowchart that illustrates an example process for storing hazardous waste material in a subterranean formation from which water has been tested for a radioactive isotope concentration percentage.

Process 300 continues at step 316, which includes storing hazardous waste material in the hazardous waste storage area. FIG. 4 illustrates an example sub-process for step 316 of process 300.

In some implementations, one or both of the subterranean formations 108 or 110 may not allow mobile water to pass therethrough or may allow mobile water to pass therethrough only at extremely low velocities. Thus, relative to the surface water formation 106, one or both of the subterranean formations 108 or 110 may have low permeability, e.g., on the order of nanodarcy permeability. Additionally, one or both of the subterranean formations 108 or 110 may be a relatively non-ductile (i.e., brittle) geologic formation. One measure of non-ductility is brittleness, which is the ratio of compressive stress to tensile strength. In some examples, the brittleness of the one or both of the subterranean formations 108 or 110 may be between about 20 MPa and 40 MPa.

In some examples, rock formations of which one or both of the subterranean formations 108 or 110 may be composed include, for example, certain kinds of sandstone, mudstone, clay, and slate that exhibit permeability and brittleness properties as described above. In some aspects, one or both of the subterranean formations 108 or 110 may be thick, e.g., between about 200 and 2000 feet of total vertical thickness. Thickness of one or both of the subterranean formations 108 or 110 may allow for easier landing and directional drilling, thereby allowing a hazardous material storage area to be readily emplaced within one or both of the subterranean formations 108 or 110 during construction (e.g., drilling). If formed through an approximate horizontal center of a particular one of the subterranean formations 108 or 110, a hazardous waste material storage area may be surrounded by about 50 to 200 feet of geologic formation.

In some aspects, one or both of the subterranean formations 108 or 110 may also have only immobile water, e.g., due to a very low permeability (e.g., on the order of micro- or nanodarcys). In addition, one or both of the subterranean formations 108 or 110 may have sufficient ductility, such that a brittleness of the rock formation is between about 3 MPa and 10 MPa. Examples of rock formations of which one or both of the subterranean formations 108 or 110 may be composed include shale and anhydrite. Further, in some aspects, hazardous waste material may be stored below one or both of the subterranean formations 108 or 110, even in a permeable formation such as sandstone or limestone, if one of the subterranean formations 108 or 110 is of sufficient geologic properties to isolate the permeable layer from the surface water formation 106.

In some examples implementations, one or both of the subterranean formations 108 or 110 is composed of shale. Shale, in some examples, may have properties that fit within those described above. For example, shale formations may be suitable for a long-term confinement of hazardous waste material, and for their isolation from surface water formation 106 and the terranean surface 102. Shale formations may be found relatively deep in the earth, typically 3000 feet or greater, and placed in isolation below any fresh water aquifers. Other formations may include salt or other impermeable formation layer.

Shale formations (or salt or other impermeable formation layers), for instance, may include geologic properties that enhance the long-term (e.g., thousands of years) isolation of material. Such properties, for instance, have been illustrated through the long-term storage (e.g., tens of millions of years) of hydrocarbon fluids (e.g., gas, liquid, mixed phase fluid) without escape of substantial fractions of such fluids into surrounding layers (e.g., surface water formation 106). Indeed, shale has been shown to hold natural gas for millions of years or more, giving it a proven capability for long-term storage of hazardous waste material. Example shale formations (e.g., Marcellus, Eagle Ford, Barnett, and otherwise) has stratification that contains many redundant sealing layers that have been effective in preventing movement of water, oil, and gas for millions of years, lacks mobile water, and can be expected (e.g., based on geological considerations) to seal hazardous waste material (e.g., fluids or solids) for thousands of years after deposit.

In some aspects, the formation of one or both of the subterranean formations 108 or 110 may form a leakage barrier, or barrier layer to fluid leakage that may be determined, at least in part, by the evidence of the storage capacity of the layer for hydrocarbons or other fluids (e.g., carbon dioxide) for hundreds of years, thousands of years, tens of thousands of years, hundreds of thousands of years, or even millions of years. For example, one or both of the subterranean formations 108 or 110 may be defined by a time constant for leakage of the hazardous waste material more than 10,000 years (such as between about 10,000 years and 1,000,000 years) based on such evidence of hydrocarbon or other fluid storage.

Shale (or salt or other impermeable layer) formations may also be at a suitable depth, e.g., between 3000 and 12,000 feet true vertical depth (TVD). Such depths are typically below ground water aquifer (e.g., surface water formation 106). Further, the presence of soluble elements in shale, including salt, and the absence of these same elements in aquifer layers, demonstrates a fluid isolation between shale and the aquifer layers.

Another particular quality of shale that may advantageously lend itself to hazardous waste material storage is its clay content, which, in some aspects, provides a measure of ductility greater than that found in other, impermeable rock formations. For example, shale may be stratified, made up of thinly alternating layers of clays (e.g., between about 20-40% clay by volume) and other minerals. Such a composition may make shale less brittle and, thus less susceptible to fracturing (e.g., naturally or otherwise) as compared to rock formations in the impermeable layer (e.g., dolomite or otherwise). For example, rock formations in the impermeable layer 108 may have suitable permeability for the long-term storage of hazardous waste material, but are too brittle and commonly are fractured. Thus, such formations may not have sufficient sealing qualities (as evidenced through their geologic properties) for the long-term storage of hazardous waste material.

The present disclosure contemplates that there may be many other layers between or among the illustrated subterranean layers 106, 108, and 110. For example, there may be repeating patterns (e.g., vertically), of one or more of the surface water formation 106 or one or both of the subterranean formations 108 or 110. Further, in some instances, the subterranean formation 108 may be directly adjacent (e.g., vertically) the surface water formation 106, i.e., without an intervening layer. In some examples, all or portions of the curved drillhole 208 and the storage drillhole 210 may be formed below one or both of the subterranean formations 108 or 110, such that the formation in which the subterranean water has been tested is vertically positioned between the storage drillhole 210 and the surface water formation 106.

In example implementations, one or both of the subterranean formations 108 or 110 may include a self-healing layer. In some aspects, a self-healing layer may comprise a geologic formation that can stop or impede a flow of hazardous waste material (whether in liquid, solid, or gaseous form) from a storage portion of the drillhole 204 to or toward the terranean surface 102. For example, during formation of the drillhole 204 (e.g., drilling), all or portions of the geologic formations 108 or 110, may be disturbed, thereby affecting or changing their geologic characteristics (e.g., permeability). A disturbed zone may surround an entire length (vertical, curved, and inclined portions) of the drillhole 204 a particular distance into the formations 108 and 110.

In certain aspects, the location of the drillhole 204 may be selected so as to be formed through a self-healing layer. For example, as shown, the drillhole 204 may be formed such that at least a portion of the access portion 206 of the drillhole 204 is formed to pass through the self-healing layer. In some aspects, the self-healing layer comprises a geologic formation that that does not sustain cracks for extended time durations even after being drilled therethrough. Examples of the geologic formation in the self-healing layer include shale with high clay content, dolomite, or salt. Cracks in such rock formations tend to heal, that is, they disappear rapidly with time due to the relative ductility of the material, and the enormous pressures that occur underground from the weight of the overlying rock on the formation in the self-healing layer. In addition to providing a "healing mechanism" for cracks that occur due to the formation of the drillhole 204 (e.g., drilling or otherwise), the self-healing layer may also provide a barrier to natural faults and other cracks that otherwise could provide a pathway for hazardous waste material leakage (e.g., fluid or solid) from the storage drillhole 210 to the terranean surface 102, the surface water formation 106, or both.

FIG. 2A is a schematic illustration of example implementations of a hazardous waste material storage repository, e.g., a subterranean location for the long-term (e.g., tens, hundreds, or thousands of years or more) but retrievable safe and secure storage of hazardous waste material, during a deposit or retrieval operation according to the present disclosure. The hazardous waste material storage repository may be formed and operated, for example, subsequent to a determination that one or both of the subterranean formations 108 or 110 are suitable based on the radioactive isotope testing of the subterranean water as described with reference to FIGS. 1 and 3.

Turning to FIG. 2A, this figure illustrates an example hazardous waste material storage repository system 200 during a deposit (or retrieval, as described below) process, e.g., during deployment of one or more canisters of hazardous waste material in a subterranean formation. As illustrated, the hazardous waste material storage repository system 200 includes a drillhole 204 formed (e.g., drilled or otherwise) from the terranean surface 102 and through the subterranean layers 106, 108, and 110. In some aspects, the drillhole 204 may be the same as test drillhole 104 shown in FIG. 1. Alternatively, drillhole 204 may be an enlarged (e.g., reamed or re-drilled) version of test drillhole 104. Alternatively, the drillhole 204 may be a separate drillhole formed through the subterranean layers 106, 108, and into 110.

The illustrated drillhole 204 is a directional drillhole in this example of hazardous waste material storage repository system 200. For instance, the drillhole 204 includes an access drillhole 206 coupled to a radiussed or curved portion 208, which in turn is coupled to storage drillhole 210. In this example, the storage drillhole 210 is horizontal. Alternatively, curved portion 208 may be eliminated and storage drillhole 210 may be a vertical drillhole that couples to vertical access drillhole 204 to forma continuous, vertical drillhole. Alternatively, the curved portion 208 may differ from a 90-degree change in direction, in which case the storage drillhole 210 might be tilted.

The illustrated drillhole 204, in this example, has a surface casing 220 positioned and set around the drillhole 204 from the terranean surface 102 into a particular depth in the earth. For example, the surface casing 220 may be a relatively large-diameter tubular member (or string of members) set (e.g., cemented) around the drillhole 204 in a shallow formation. As used herein, "tubular" may refer to a member that has a circular cross-section, elliptical cross-section, or other shaped cross-section. For example, in this implementation of the hazardous waste material storage repository system 200, the surface casing 220 extends from the terranean surface through a surface layer 106. In some aspects, the surface casing 220 may isolate the drillhole 204 from surface water sources, and may also provide a hanging location for other casing strings to be installed in the drillhole 204.

As illustrated, a production casing 222 is positioned and set within the drillhole 204 downhole of the surface casing 220. Although termed a "production" casing, in this example, the casing 222 may or may not have been subject to hydrocarbon production operations. Thus, the casing 222 refers to and includes any form of tubular member that is placed in the drillhole 204 downhole of the surface casing 220. In some examples of the hazardous waste material storage repository system 200, the production casing 222 may begin at an end of the radiussed portion 108 and extend throughout the inclined portion 110. The casing 222 could also extend into the radiussed portion 108 and into the vertical portion 106.

As shown, cement 230 is positioned (e.g., pumped) around the casings 220 and 222 in an annulus between the casings 220 and 222 and the drillhole 204. The cement 230, for example, may secure the casings 220 and 222 (and any other casings or liners of the drillhole 204) through the subterranean formations under the terranean surface 102. In some aspects, the cement 230 may be installed along the entire length of the casings (e.g., casings 220 and 222 and any other casings), or the cement 230 could be used along certain portions of the casings if adequate for a particular drillhole 204. In some aspects the cement may be omitted altogether. The cement 230, if used, can also provide an additional layer of confinement for the hazardous waste material in canisters 226.

The storage drillhole portion 210 of the drillhole 204 includes a storage area in a distal part of the portion 210 into which hazardous waste material may be retrievably placed for long-term storage. For example, as shown, a work string 224 (e.g., tubing, coiled tubing, wireline, or otherwise) may be extended into the cased drillhole 204 to place one or more (three shown but there may be more or less) hazardous waste material canisters 226 into long-term, but in some aspects, retrievable, storage in the portion 210. For example, in the implementation shown in FIG. 2A, the work string 224 may include a downhole tool 228 that couples to the canister 226, and with each trip into the drillhole 204, the downhole tool 228 may deposit a particular hazardous waste material canister 226 in the storage drillhole portion 210.

The downhole tool 228 may couple to the canister 226 by, in some aspects, a threaded connection or other type of connection, such as a latched connection. In alternative aspects, the downhole tool 228 may couple to the canister 226 with an interlocking latch, such that rotation (or linear movement or electric or hydraulic switches) of the downhole tool 228 may latch to (or unlatch from) the canister 226. In alternative aspects, the downhole tool 228 may include one or more magnets (e.g., rare earth magnets, electromagnets, a combination thereof, or otherwise) which attractingly couple to the canister 226. In some examples, the canister 226 may also include one or more magnets (e.g., rare earth magnets, electromagnets, a combination thereof, or otherwise) of an opposite polarity as the magnets on the downhole tool 228. In some examples, the canister 226 may be made from or include a ferrous or other material attractable to the magnets of the downhole tool 228. Alternative techniques for moving the canisters 226 may also be used.

FIG. 2A also illustrates an example of a retrieval operation of hazardous waste material in the storage drillhole portion 210 of the drillhole 204. A retrieval operation may be the opposite of a deposit operation, such that the downhole tool 228 (e.g., a fishing tool) may be run into the drillhole 204, coupled to the last-deposited canister 226 (e.g., threadingly, latched, by magnet, or otherwise), and pull the canister 226 to the terranean surface 102. Multiple retrieval trips may be made by the downhole tool 228 in order to retrieve multiple canisters from the storage drillhole portion 210 of the drillhole 204.

Each canister 226 may enclose hazardous waste material. Such hazardous waste material, in some examples, may be biological or chemical waste or other biological or chemical hazardous waste material. In some examples, the hazardous waste material may include nuclear material, such as spent nuclear fuel recovered from a nuclear reactor (e.g., commercial power or test reactor) or defense nuclear material. For example, a gigawatt nuclear plant may produce 30 tons of spent nuclear fuel per year. The density of that fuel is typically close to 10 (10 $gm/cm^3$=10 kg/liter), so that the volume for a year of nuclear waste is about 3 $m^3$. Spent nuclear fuel, in the form of nuclear fuel pellets, may be taken from the reactor and not modified. Nuclear fuel pellet are solid, although they can contain and emit a variety of radioactive gases including tritium (13 year half-life), krypton-85 (10.8 year half-life), and carbon dioxide containing C-14 (5730 year half-life).

In some aspects, one or both of the subterranean formations 108 or 110 may contain any radioactive output (e.g., gases) therewithin, even if such output escapes the canisters 226. For example, one or both of the subterranean formations 108 or 110 may be shown to contain radioactive output based on the test results of the subterranean water testing as described with reference to FIGS. 1 and 3.

Other criteria in addition to the subterranean water testing as described herein may be used to determine that the subterranean formations 108 or 110 contain any radioactive output (e.g., gases) therewithin. For example, one or both of the subterranean formations 108 or 110 may be selected based on diffusion times of radioactive output through the formations 108 or 110. For example, a minimum diffusion time of radioactive output escaping the subterranean formations 108 or 110 may be set at, for example, fifty times a half-life for any particular component of the nuclear fuel pellets. Fifty half-lives as a minimum diffusion time would reduce an amount of radioactive output by a factor of $1\times10^{15}$. As another example, setting a minimum diffusion time to thirty half-lives would reduce an amount of radioactive output by a factor of one billion.

For example, plutonium-239 is often considered a dangerous waste product in spent nuclear fuel because of its long half-life of 24,200 years. For this isotope, 50 half-lives would be 1.2 million years. Plutonium-239 has low solubility in water, is not volatile, and as a solid, its diffusion time is exceedingly small (e.g., many millions of years) through a matrix of the rock formation that comprise the illustrated subterranean formations 108 or 110 (e.g., shale or other formation). The subterranean formations 108 or 110, for example comprised of shale, may offer the capability to have such isolation times (e.g., millions of years) as shown by the geological history of containing gaseous hydrocarbons (e.g., methane and otherwise) for several million years. In contrast, in conventional nuclear material storage methods, there was a danger that some plutonium might dissolve in a layer that comprised mobile ground water upon confinement escape.

In some aspects, the drillhole 204 may be formed for the primary purpose of long-term storage of hazardous waste materials. In alternative aspects, the drillhole 204 may have been previously formed for the primary purpose of hydrocarbon production (e.g., oil, gas). For example, one or both of subterranean formations 108 or 110 may be a hydrocarbon bearing formation from which hydrocarbons were produced into the drillhole 204 and to the terranean surface 102. In some aspects, the subterranean formations 108 or 110 may have been hydraulically fractured prior to hydrocarbon production. Further in some aspects, the production casing 222 may have been perforated prior to hydraulic fracturing. In such aspects, the production casing 222 may be patched (e.g., cemented) to repair any holes made from the perforating process prior to a deposit operation of hazardous waste material. In addition, any cracks or openings in the cement between the casing and the drillhole can also be filled at that time.

For example, in the case of spent nuclear fuel as a hazardous waste material, the drillhole may be formed at a particular location, e.g., near a nuclear power plant, as a new drillhole provided that the location also includes an appropriate subterranean formation 108 or 110, such as a shale formation. Alternatively, an existing well that has already produced shale gas, or one that was abandoned as "dry," (e.g., with sufficiently low organics that the gas in place is too low for commercial development), may be selected as the drillhole 204. In some aspects, prior hydraulic fracturing of the subterranean formations 108 or 110 through the drillhole 204 may make little difference in the hazardous waste material storage capability of the drillhole 204. But such a prior activity may also confirm the ability of one or both of the subterranean formations 108 or 110 to store gases and other fluids for millions of years. If, therefore, the hazardous waste material or output of the hazardous waste material (e.g., radioactive gasses or otherwise) were to escape from the canister 226 and enter the fractured formation of the subterranean formations 108 or 110, such fractures may allow that material to spread relatively rapidly over a distance comparable in size to that of the fractures. In some aspects, the drillhole 204 may have been drilled for a production of hydrocarbons, but production of such hydrocarbons had failed, e.g., because one or both of the subterranean formations 108 or 110 comprised a rock formation (e.g., shale or otherwise) that was too ductile and difficult to fracture for production, but was advantageously ductile for the long-term storage of hazardous waste material.

Figure 2B:
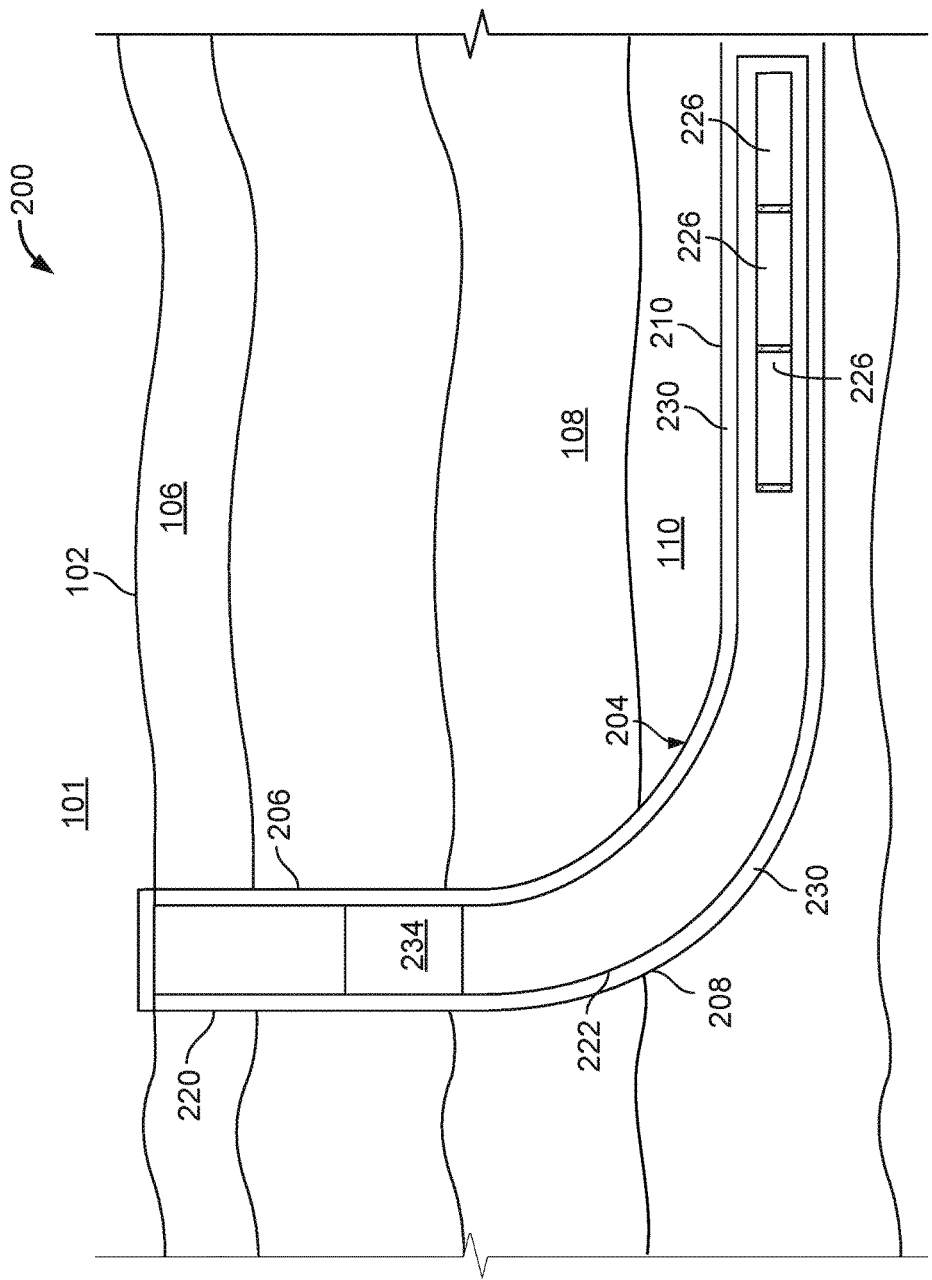
FIG. 2B is a schematic illustration of an example implementation of a hazardous waste material storage repository system during storage of hazardous waste material.

FIG. 2B is a schematic illustration of an example implementation of the hazardous waste material storage repository 200 during storage and monitoring operations according to the present disclosure. For example, FIG. 2B illustrates the hazardous waste material storage repository 200 in a long-term storage operation. One or more hazardous waste material canisters 226 are positioned in the storage drillhole portion 210 of the drillhole 204. A seal 234 is placed in the drillhole 204 between the location of the canisters 226 in the storage drillhole portion 210 and an opening of the access drillhole 206 at the terranean surface 102 (e.g., a well head). In this example, the seal 234 is placed at an uphole end of the curved portion 108. Alternatively, the seal 234 may be positioned at another location within the access drillhole 206, in the curved portion 208, or even within the storage drillhole portion 210 uphole of the canisters 226. In some aspects, the seal 234 may be placed at least deeper than any source of surface water, such as the surface water formation 106. In some aspects, the seal 234 may be formed substantially along an entire length of the access drillhole 206.

As illustrated, the seal 234 fluidly isolates the volume of the storage drillhole 110 that stores the canisters 226 from the opening of the access drillhole 206 at the terranean surface 102. Thus, any hazardous waste material (e.g., radioactive material) that does escape the canisters 226 may be sealed (e.g., such that liquid, gas, or solid hazardous waste material) does not escape the drillhole 104. The seal 234, in some aspects, may be a cement plug or other plug, that is positioned or formed in the drillhole 204. As another example, the seal 234 may be formed from one or more inflatable or otherwise expandable packers positioned in the drillhole 204. As another example, the seal 234 may be formed of a combination of rock and bentonite. As another example, the seal 234 may be formed from rock similar in composition to the rock found in nearby layers, such as clay-rich shale.

Prior to a retrieval operation (e.g., as discussed with reference to FIG. 2A), the seal 234 may be removed. For example, in the case of a cement or other permanently set seal 234, the seal 234 may be drilled through or otherwise milled away. In the case of semi-permanent or removable seals, such as packers, the seal 234 may be removed from the drillhole 204 through a conventional process as is known.

Monitoring operations may be performed during long-term storage of the canisters 226. For example, in some aspects, it may be advantageous or required to monitor one or more variables during long-term storage of the hazardous waste material in the canisters 226. In an example, a monitoring system includes one or more sensors placed in the drillhole 204 (e.g., within the storage drillhole 210) and communicably coupled to a monitoring control system through a cable (e.g., electrical, optical, hydraulic, or otherwise) or through a non-cable method (e.g. acoustic signals). The sensors may be placed outside of the casings, or even built into the casings before the casings are installed in the drillhole 204. Sensors could also be placed outside the casing.

The sensors may monitor one or more variables, such as, for example, radiation levels, temperature, pressure, presence of oxygen, a presence of water vapor, a presence of liquid water, acidity, seismic activity, or a combination thereof. Data values related to such variables may be transmitted along the cable to the monitoring control system. The monitoring control system, in turn, may record the data, determine trends in the data (e.g., rise of temperature, rise of radioactive levels), send data to other monitoring locations, such as national security or environmental center locations, and may further automatically recommend actions (e.g., retrieval of the canisters 226) based on such data or trends. For example, a rise in temperature or radioactive level in the drillhole 204 above a particular threshold level may trigger a retrieval recommendation, e.g., to ensure that the canisters 226 are not leaking radioactive material. In some aspects, there may be a one-to-one ratio of sensors to canisters 226. In alternative aspects, there may be multiple sensors per canister 226, or there may be fewer.

FIG. 4 is a flowchart that illustrates an example implementation of step 316 for storing hazardous waste material in a subterranean formation from which water has been tested for a radioactive isotope concentration percentage. Step 316 may begin with sub-step 402, which includes which includes moving a storage canister through an entry of a drillhole that extends into a terranean surface. The storage canister encloses a hazardous waste material, such as chemical, biological, or nuclear waste, or another hazardous waste material. In some aspects, the storage canister may be positioned in the entry directly from a mode of transportation (e.g., truck, train, rail, or otherwise) which brought the hazardous waste material to the site of the drillhole. In some aspects, a packaging of the hazardous waste material during transport is not removed for movement of the storage canister into the entry. In some aspects, such transport packaging is only removed as the storage canister fully enters the drillhole.

Step 316 may continue at sub-step 404, which includes moving the storage canister through the drillhole that includes a substantially vertical portion, a transition portion, and a substantially horizontal portion. In some aspects, the drillhole is a directional, or slant drillhole. The storage canister may be moved through the drillhole in a variety of manners. For example, a tool string (e.g., tubular work string) or wireline may include a downhole tool that couples to the storage canister and moves (e.g., pushes) the storage canister from the entry to the horizontal portion of the drillhole. As another example, the storage canister may ride on rails installed in the drillhole, e.g., a cased drillhole. As yet another example, the storage canister may be moved through the drillhole with a drillhole tractor (e.g., motored or powered tractor). In another example, the tractor could be built as part of the storage canister. As yet a further example, the storage canister may be moved through the drillhole with a fluid (e.g., gas or liquid) circulated through the drillhole.

Step 316 may continue at sub-step 406, which includes moving the storage canister into a storage area located within or below a shale formation. For example, the horizontal portion of the drillhole may include or be coupled to the storage area and may be formed through a shale seam within a subterranean zone. In some aspects, the shale may include one or more geologic qualities that provide for a fluidic seal (e.g., gas and liquid) against the escape of any hazardous waste material beyond the shale formation (e.g., vertically or horizontally). In alternative aspects, the storage area may be formed in the horizontal portion of the drillhole in a rock formation that is not shale, but shares particular geologic characteristics with shale (e.g., anhydrite, and other formations). For example, the rock formation of the storage area may be relatively impermeable, with permeability values less than 0.001 millidarcys (and even down to nanodarcys). As another example, the rock formation may be ductile, having a brittleness of less than about 10 MPa so as to prevent or help prevent fracturing that can allow hazardous waste material leaks therethrough. Brittleness, as used herein in example implementations, is the ratio of compressive stress of the rock formation to tensile strength of the rock formation. As another example, the rock formation may be relatively thick, with thickness proximate the storage area of between about 100 and 200 feet (although less thick and more thick formations are also contemplated by the present disclosure). As another example, the rock formation may be composed of clay or other organic material, e.g., of about 20-40% weight by volume, to help ductility. As another example, the rock formation may be composed of salt.

Step 316 may continue at sub-step 408, which includes forming a seal in the drillhole that isolates the storage portion of the drillhole from the entry of the drillhole. For example, once the storage canister is moved into the storage area (or after all storage canisters are moved into the storage area), a seal may be formed in the drillhole. The seal may be a cement plug, an inflatable seal (e.g., packer), a region containing a mixture of rock and bentonite, or other seal or combination of such seals. In some aspects, the seal is removable so as to facilitate a subsequent retrieval operation of the storage canister.

Step 316 may continue at sub-step 410, which includes monitoring at least one variable associated with the storage canister from a sensor positioned proximate the storage area. The variable may include one or more of temperature, radioactivity, seismic activity, oxygen, water vapor, acidity, or other variable that indicates a presence of the hazardous waste material (e.g., within the drillhole, outside of the storage canister, in the rock formation, or otherwise). In some aspects, one or more sensors may be positioned in the drillhole, on or attached to the storage canister, within a casing installed in the drillhole, or in the rock formation proximate the drillhole. The sensors, in some aspects, may also be installed in a separate drillhole (e.g., another horizontal or vertical drillhole) apart from the storage area.

Step 316 may continue at sub-step 412, which includes recording the monitored variable at the terranean surface. For example, variable data received at the one or more sensors may be transmitted (e.g., on a conductor or wirelessly) to a monitoring system at the terranean surface. The monitoring system may perform a variety of operations. For example, the monitoring system may record a history of one or more of the monitored variables. The monitoring system may provide trend analysis in the recorded variable data. As another example, the monitoring system may include one or more threshold limits for each of the monitored variables, and provide an indication when such threshold limits are exceeded.

Step 316 may continue at sub-step 414, which includes determining whether the monitored variable exceeds a threshold value. For example, the one or more sensors may monitor radioactivity in the drillhole, e.g., an amount of radiation emitted by the hazardous waste material, whether in alpha or beta particles, gamma rays, x-rays, or neutrons. The sensors, for instance, may determine an amount of radioactivity, in units of measure of curie (Ci) and/or becquerel (Bq), rads, grays (Gy), or other units of radiation. If the amount of radioactivity does not exceed a threshold value that, for example, would indicate a large leak of hazardous nuclear material from the storage canister, then the step 316 may return to sub-step 410.

If the determination is "yes," sub-step 316 may continue at sub-step 416, which includes removing the seal from the drillhole. For example, in some aspects, once a threshold value (or values) is exceeded, a retrieval operation may be initiated by removing the seal. In alternative aspects, exceeding of a threshold value may not automatically trigger a retrieval operation or removal of the drillhole seal. In some aspects, there may be multiple monitored variables, and a "yes" determination is only made if all monitored variables exceed their respective threshold values. Alternatively, a "yes" determination may be made if at least one monitored variable exceeds its respective threshold value.

Step 316 may continue at sub-step 418, which includes retrieving the storage canister from the storage area to the terranean surface. For example, once the seal is removed (e.g., drilled through or removed to the terranean surface), the work string may be tripped into the drillhole to remove the storage canister for inspection, repair, or otherwise. In some aspects, rather than removing the seal from the drillhole to retrieve the storage canister, other remedial measures may be taken. For example, if the determination is "yes" in sub-step 414, rather than recovering the hazardous waste material, a decision might be made to improve the seal. This could be done, for example, by injecting bentonite, a cement, or other sealant into the borehole to fill the space previously filled with gas.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

What is claimed is:

1. A method, comprising:
   collecting, from a test drillhole formed from a terranean surface to a subterranean formation, a subterranean water sample from the subterranean formation;
   determining, with an accelerator mass spectrometry (AMS) system, a concentration of a radioactive isotope of an element in the subterranean water sample relative to a stable isotope of the element in the subterranean water sample;
   comparing the determined concentration of the radioactive isotope of the element in the subterranean water sample with a concentration of the radioactive isotope of the element in a surface water sample relative to the stable isotope of the element in the surface water sample;
   based on the determined concentration of the radioactive isotope in the subterranean water sample being a specified percentage of the concentration of the radioactive isotope in the surface water sample, determining that the subterranean formation is suitable as a hazardous waste storage repository; and
   based on the determination that the subterranean formation is suitable as the hazardous waste storage repository, forming an access drillhole from the terranean surface toward the subterranean formation.

2. The method of claim 1, wherein:
   the radioactive isotope is carbon-14 ($^{14}C$) and the stable isotope is $^{12}C$ or $^{13}C$;
   the radioactive isotope is chlorine-36 ($^{36}Cl$) and the stable isotope is $^{35}Cl$;
   the radioactive isotope is iodine-129 ($^{129}I$) and the stable isotope is $^{127}I$;
   the radioactive isotope is beryllium-10 ($^{10}Be$) and the stable isotope is $^9Be$; or
   the radioactive isotope is aluminum-26 ($^{26}Al$) and the stable isotope is $^{27}Al$.

3. The method of claim 1, wherein the specified percentage is less than 50 percent.

4. The method of claim 1, further comprising collecting the surface water sample from a surface water source.

5. The method of claim 4, wherein the surface water source comprises at least one of an aquifer or a water source at the terranean surface in contact with the earth's atmosphere.

6. The method of claim 1, wherein the surface water sample comprises potable water.

7. The method of claim 1, wherein collecting the subterranean water sample from the subterranean formation comprises:
   operating a downhole tool in the test drillhole to collect a core sample from the subterranean formation;
   retrieving the core sample to the terranean surface; and
   removing water from the core sample, the removed water comprising the subterranean water sample.

8. The method of claim 4, wherein collecting the surface water sample from the surface water source is performed prior in time to collecting the subterranean water sample from the subterranean formation.

9. The method of claim 1, wherein the subterranean formation comprises a shale formation.

10. The method of claim 1, wherein the subterranean formation comprises a permeability of less than about 0.01 millidarcys.

11. The method of claim 1, further comprising forming the test drillhole from the terranean surface to the subterranean formation.

12. The method of claim 1, wherein the test drillhole comprises a vertical drillhole.

13. The method of claim 1, wherein the subterranean formation comprises a brittleness of less than about 10 MPa, where brittleness comprises a ratio of compressive stress of the subterranean formation to tensile strength of the subterranean formation.

14. The method of claim 1, wherein the subterranean formation comprises about 20 to 40% weight by volume of clay or organic matter.

15. The method of claim 1, wherein the subterranean formation comprises an impermeable layer.

16. The method of claim 1, wherein the subterranean formation comprises a leakage barrier defined by a time constant for leakage of a hazardous waste material of 10,000 years or more.

17. The method of claim 1, wherein the subterranean formation comprises a hydrocarbon or carbon dioxide bearing formation.

18. The method of claim 1, further comprising initiating creation of the hazardous waste storage repository in or under the subterranean formation.

19. The method of claim 18, wherein initiating creation of the hazardous waste storage repository in or under the subterranean formation comprises:
   forming a storage drillhole coupled to the access drillhole in or under the subterranean formation, the storage drillhole comprising a hazardous waste storage area.

20. The method of claim 19, wherein the access drillhole comprises a vertical drillhole.

21. The method of claim 19, wherein the test drillhole comprises a portion of the access drillhole.

22. The method of claim 19, wherein the storage drillhole comprises a curved portion and a horizontal portion.

23. The method of claim 19, wherein the subterranean formation comprises a thickness proximate the hazardous waste material storage area of at least about 200 feet.

24. The method of claim 19, wherein the subterranean formation comprises a thickness proximate the hazardous waste material storage area that inhibits diffusion of a hazardous waste material through the subterranean formation for an amount of time that is based on a half-life of the hazardous waste material.

25. The method of claim 19, further comprising installing a casing in the access drillhole and the storage drillhole that extends from at or proximate the terranean surface, through the access drillhole and the storage drillhole, and into the hazardous waste material storage area of the storage drillhole.

26. The method of claim 25, further comprising cementing the casing to the access drillhole and the storage drillhole.

27. The method of claim 19, further comprising, subsequent to forming the access drillhole, producing hydrocarbon fluid from the subterranean formation, through the access drillhole, and to the terranean surface.

28. The method of claim 19, further comprising storing hazardous waste material in the hazardous waste storage area.

29. The method of claim 28, wherein storing hazardous waste material in the hazardous waste storage area comprises:
    moving a storage canister through an entry of the access drillhole that extends into the terranean surface, the entry at least proximate the terranean surface, the storage canister comprising an inner cavity sized to enclose the hazardous waste material;
    moving the storage canister through the access drillhole and into the storage drillhole; and
    moving the storage canister through the storage drillhole to the hazardous waste storage area.

30. The method of claim 29, further comprising forming a seal in at least one of the access drillhole or the storage drillhole that isolates the hazardous waste storage area from the entry of the access drillhole.

31. The method of claim 28, wherein the hazardous waste material comprises spent nuclear fuel.

32. The method of claim 29, wherein the storage canister comprises a connecting portion configured to couple to at least one of a downhole tool string or another storage canister.

33. The method of claim 29, further comprising monitoring the hazardous waste material stored in the hazardous waste material storage area of the storage drillhole.

34. The method of claim 33, wherein monitoring the hazardous waste material stored in the hazardous waste material storage area of the storage drillhole comprises:
    removing the seal; and
    retrieving the storage canister from the hazardous waste material storage area to the terranean surface.

35. The method of claim 33, wherein monitoring the hazardous waste material stored in the hazardous waste material storage area of the storage drillhole comprises:
    monitoring at least one variable associated with the storage canister from a sensor positioned proximate the hazardous waste material storage area; and
    recording the monitored variable at the terranean surface.

36. The method of claim 35, wherein the monitored variable comprises at least one of radiation level, temperature, pressure, presence of oxygen, presence of water vapor, presence of liquid water, acidity, or seismic activity.

37. The method of claim 36, further comprising, based on the monitored variable exceeding a threshold value:
    removing the seal; and
    retrieving the storage canister from the hazardous waste material storage drillhole portion to the terranean surface.

* * * * *